(12) United States Patent
Arayama et al.

(10) Patent No.: US 9,144,521 B2
(45) Date of Patent: Sep. 29, 2015

(54) DISPOSABLE WEARING ARTICLE WITH CENTRAL AND SIDE CURVING PORTIONS

(75) Inventors: Takaya Arayama, Kagawa (JP); Hirotomo Mukai, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 359 days.

(21) Appl. No.: 13/580,538

(22) PCT Filed: Feb. 25, 2011

(86) PCT No.: PCT/JP2011/001122
§ 371 (c)(1),
(2), (4) Date: Oct. 12, 2012

(87) PCT Pub. No.: WO2011/105109
PCT Pub. Date: Sep. 1, 2011

(65) Prior Publication Data
US 2013/0030398 A1 Jan. 31, 2013

(30) Foreign Application Priority Data
Feb. 27, 2010 (JP) .................. 2010-043596

(51) Int. Cl.
*A61F 13/47* (2006.01)
*A61F 13/53* (2006.01)
(Continued)

(52) U.S. Cl.
CPC ......... *A61F 13/49001* (2013.01); *A61F 13/535* (2013.01); *A61F 2013/5307* (2013.01); *A61F 2013/53051* (2013.01)

(58) Field of Classification Search
CPC . A61F 13/532; A61F 13/5323; A61F 13/533; A61F 13/534; A61F 13/535; A61F 13/536; A61F 13/4756; A61F 13/4704; A61F 13/47218; A61F 13/53708; A61F 2013/530481; A61F 2013/53051; A61F 2013/51078; A61F 2013/53778
USPC .................. 604/367, 368, 379, 380, 385.101
See application file for complete search history.

(56) References Cited

U.S. PATENT DOCUMENTS 5,460,623 A 10/1995 Emenaker et al.
5,569,231 A 10/1996 Emenaker et al.
(Continued)

FOREIGN PATENT DOCUMENTS

EP 692232 A1 1/1996
JP 539691 Y2 10/1993
(Continued)

OTHER PUBLICATIONS

International Search Report and Written Opinion for PCT/JP2011/001122 mailed May 31, 2011.
(Continued)

*Primary Examiner* — Lynne Anderson
*Assistant Examiner* — Kathryn E Ditmer
(74) *Attorney, Agent, or Firm* — Lowe Hauptman & Ham, LLP

(57) ABSTRACT

A disposable diaper has a central slit formed along the lengthwise direction L so that the absorber can be curved to be convex in the inward direction, and a pair of side slits formed along the lengthwise direction L so that the absorber can be curved to be convex in the outward direction. An average total weight of a water absorbent polymer at the central portion CT and the side edge portion $S_L$, $S_R$ is smaller than an average total weight of the water absorbent polymer at the middle portion $M_L$, $M_R$.

8 Claims, 12 Drawing Sheets

(51) Int. Cl.
   *A61F 13/534* (2006.01)
   *A61F 13/49* (2006.01)
   *A61F 13/535* (2006.01)

(56) References Cited

U.S. PATENT DOCUMENTS

| | | | |
|---|---|---|---|
| 5,846,231 A * | 12/1998 | Fujioka et al. | 604/380 |
| 6,160,197 A | 12/2000 | Lassen et al. | |
| 6,410,822 B1 * | 6/2002 | Mizutani | 604/380 |
| 6,521,811 B1 | 2/2003 | Lassen et al. | |
| 2001/0007936 A1 | 7/2001 | Shimoe et al. | |
| 2002/0013563 A1 | 1/2002 | Lassen et al. | |
| 2002/0065498 A1 * | 5/2002 | Ohashi et al. | 604/379 |
| 2004/0243081 A1 * | 12/2004 | Suzuki et al. | 604/378 |
| 2006/0069371 A1 * | 3/2006 | Ohashi et al. | 604/385.01 |
| 2006/0116653 A1 * | 6/2006 | Munakata et al. | 604/380 |
| 2006/0264859 A1 | 11/2006 | Tsuji et al. | |
| 2008/0140042 A1 | 6/2008 | Mukai et al. | |
| 2010/0022978 A1 | 1/2010 | Kasai et al. | |

FOREIGN PATENT DOCUMENTS

| | | |
|---|---|---|
| JP | 7328063 | 12/1995 |
| JP | 9509600 | 9/1997 |
| JP | 10234775 A | 9/1998 |
| JP | 2001190592 | 7/2001 |
| JP | 2001190592 A | 7/2001 |
| JP | 2002209940 | 7/2002 |
| JP | 200441311 A | 2/2004 |
| JP | 2004041311 A * | 2/2004 |
| JP | 3616077 B2 | 2/2005 |
| JP | 2006115996 A | 5/2006 |
| JP | 2006346439 | 12/2006 |
| JP | 2006346439 A | 12/2006 |
| JP | 200729507 A | 2/2007 |
| JP | 2008284190 A | 11/2008 |
| JP | 2011104021 A | 6/2011 |
| JP | 2011177308 A | 9/2011 |
| WO | 9402092 | 2/1994 |
| WO | 9925284 | 5/1999 |
| WO | 2008069279 | 6/2008 |
| WO | 2008069279 A1 | 6/2008 |

OTHER PUBLICATIONS

Extended European Search Report issued Dec. 20, 2013, corresponds to European patent application No. 11747073.2.
Office Action mailed Sep. 3, 2013, corresponds to Japanese patent application No. 2010-043596.
Office Action issued Jan. 30, 2015, corresponding to Australian patent application No. 2011219337.
Office Action mailed Aug. 26, 2014, corresponds to Japanese patent application No. 2013-226622.

* cited by examiner

DISPOSABLE WEARING ARTICLE WITH CENTRAL AND SIDE CURVING PORTIONS

RELATED APPLICATIONS

The application is a national phase of PCT/JP2011/001122, filed Feb. 25, 2011 and is based on, and claims priority from, Japanese Application Number 2010-043596, filed Feb. 27, 2010.

TECHNICAL FIELD

The present disclosure relates to a disposable wearing article which is provided with an absorber including a water absorbent polymer, wherein a curve forming portion for curving the absorber is formed at the absorber.

BACKGROUND ART

In disposable wearing articles such as pant-type diapers, a variety of contrivances are made in order to improve the feeling of a wearer or prevent leakage of bodily waste. For example, there is known a pant-type diaper in which three curve forming portions are formed along a lengthwise direction of an absorber at the absorber for absorbing bodily waste of a wearer (Japanese Patent Application Publication No. 2006-346439, for example).

Specifically, in this pant-type diaper, three slits are formed at the absorber, and peripheral portions of the slits each are curved. The central slit peripheral portion is formed to be convex toward an excretion portion of the wearer. In addition, a lateral slit peripheral portion is formed to be convex at an opposite side of the central slit peripheral portion. Namely, a cross-cross-sectional shape of the absorber along a widthwise direction of the absorber is deformed in a W-letter shape.

Thus, the convex portion of the absorber, which is formed by the central slit peripheral portion, easily comes into intimate contact with a wearer's excretion portion. In addition, bodily waste easily enters a concave portion which is formed by two outside slit peripheral portions to be thereby able to restrain bodily waste from coming into direct contact with the wearer's skin.

SUMMARY OF INVENTION

However, if the amount of the water absorbent polymer that is included in the absorber is increased in an attempt to improve absorptive power of the conventional pant-type diaper described above, the following problem occurs. That is, if an absorber of which basis weight of the water absorbent polymer is large absorbs bodily waste, the absorber swells greatly and then becomes thick, and a wearer easily has an uncomfortable feeling if his or her legs are closed, for example, at the time of taking a standing position.

In addition, the absorber is positioned in a state in which it is curved at a wearer's crotch portion, and thus, if the absorber swells, it cannot be sufficiently curved, and the absorber hardly comes into contact with the wearer's excretion portion. Thus, there has still remained unsolved the problem that urine or watery stool or the like easily leaks to the outside with it going along the wearer's skin.

Therefore, it is an object of the present invention to provide a disposable wearing article, such as a pant-type diaper, which is capable of more reliably restraining an uncomfortable feeling of a wearer even after absorption of bodily waste or leakage of bodily waste while further improving absorptive power.

A disposable wearing article according to the present invention in a first aspect includes an absorber having: a lengthwise direction; a widthwise direction which is orthogonal to the lengthwise direction; an inward direction which is oriented to a wearer; and an outer direction which is oriented to a side opposite to the inward direction, the absorber including a water absorbent polymer. The absorber has, in a crotch portion region applied to a crotch portion of the wearer, a central portion which is formed at a central part of the absorber in the widthwise direction, a pair of side edge portions including a side edge of the absorber in the widthwise direction, and a pair of middle portions which are positioned between the central portion and the side edge portion; at the central portion, a central curve forming portion is formed along the lengthwise direction so that the absorber can be curved to be convex in the inward direction; at the middle portion, a pair of side curve forming portions are formed along the lengthwise direction so that the absorber can be curved to be convex in the outward direction; and an average basis weight of a water absorbent polymer at the central portion and the side edge portion is smaller than an average basis weight of the water absorbent polymer at the middle portion.

According to the characteristics of the present invention, there can be provided a disposable wearing article, such as a pant-type diaper, featuring the absorber, which is capable of more reliably restraining an uncomfortable feeling of a wearer even after absorption of bodily waste or leakage of bodily waste while further improving absorptive power.

DESCRIPTION OF EMBODIMENT

Figure 1:
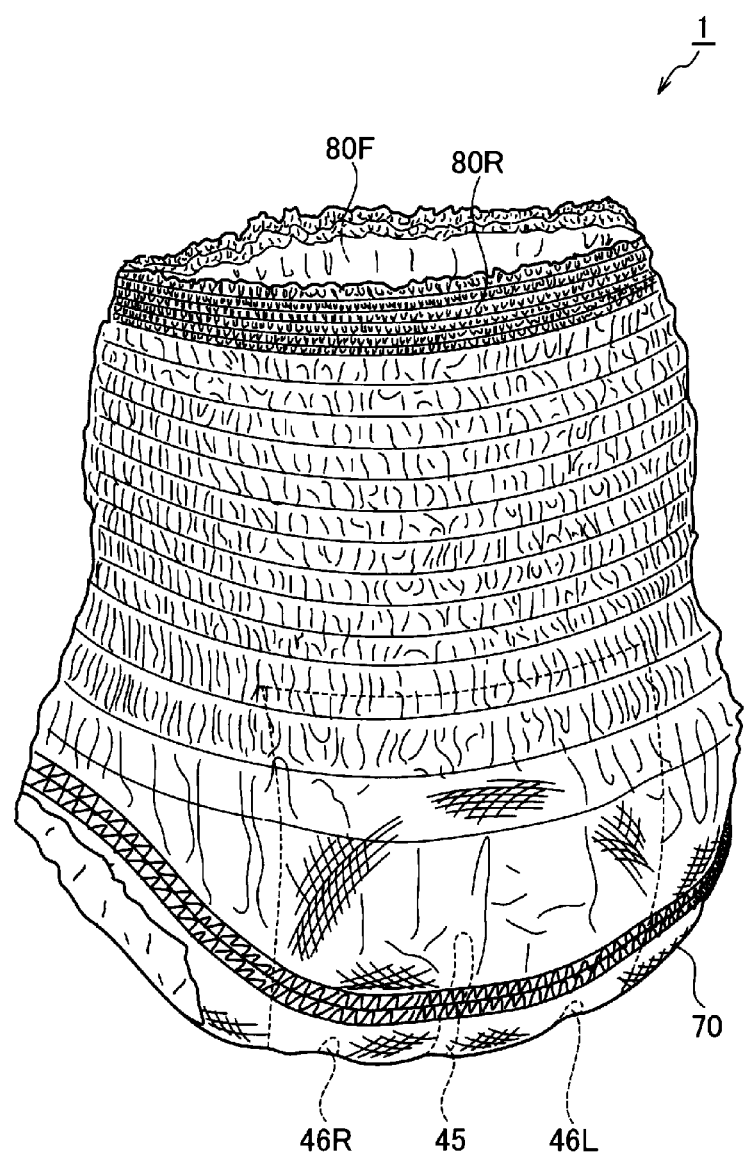
FIG. 1 is a schematic perspective view of a diaper 1 according to a first embodiment.

Next, the embodiments of a disposable wearing article comprising the absorber, according to the present invention, will be described with reference to the drawings. In the description of drawings that follow, the same or like constituent elements are designated by the same or like reference numerals. However, it should be kept in mind that the drawings are schematic and ratios or the like of dimensions each may be different from an actual one.

Therefore, specific dimensions or the like should be determined in consideration of the following description. In addition, portions with different dimensional interrelationships or ratios can be included in the drawings as well.

First Embodiment

A disposable wearing article according to the embodiment is provided with a central curve forming portion and a pair of side curve forming portions, and is characterized in that an average basis weight of a water absorbent polymer at a central portion, which is a region including a position of the central curve forming portion, and at a side edge portion, which is a region including a side edge of the absorber, is less than the average basis weight of the water absorbent polymer at a middle portion, which includes the side curve forming portions.

(1) Entire Schematic Configuration of Disposable Wearing Article

FIG. 1 is a schematic perspective view of a disposable diaper 1, which comprises a. As shown in FIG. 1, the disposable diaper 1 is a pant-type disposable diaper. The disposable diaper 1 is provided with: an exterior topsheet 70, a foreside exterior backsheet 80F and a backside exterior backsheet 80R, which configure an exterior portion of the disposable diaper 1. An absorber 40 comprised of a cotton-like pulp and a highly polymerized water absorbent polymer (hereinafter, referred to as a water absorbent polymer) is provided inside (on a skin contact surface side) of the external top sheet 70.

A plurality of curve forming portions are formed in the absorber 40. In the depicted arrangement these curve forming portions comprise slits, however, the curve forming portions may take other forms, as will be readily appreciated by those skilled in the art. A central slit 45 is formed at a center in a widthwise direction of the absorber 40. In addition, a side slit 46L and a side slit 46R are formed one either side of the central slit 45. By means of these slits that are formed at the absorber 40, the absorber 40 is configured so that it can be curved when the disposable diaper 1 is worn.

Figure 2:
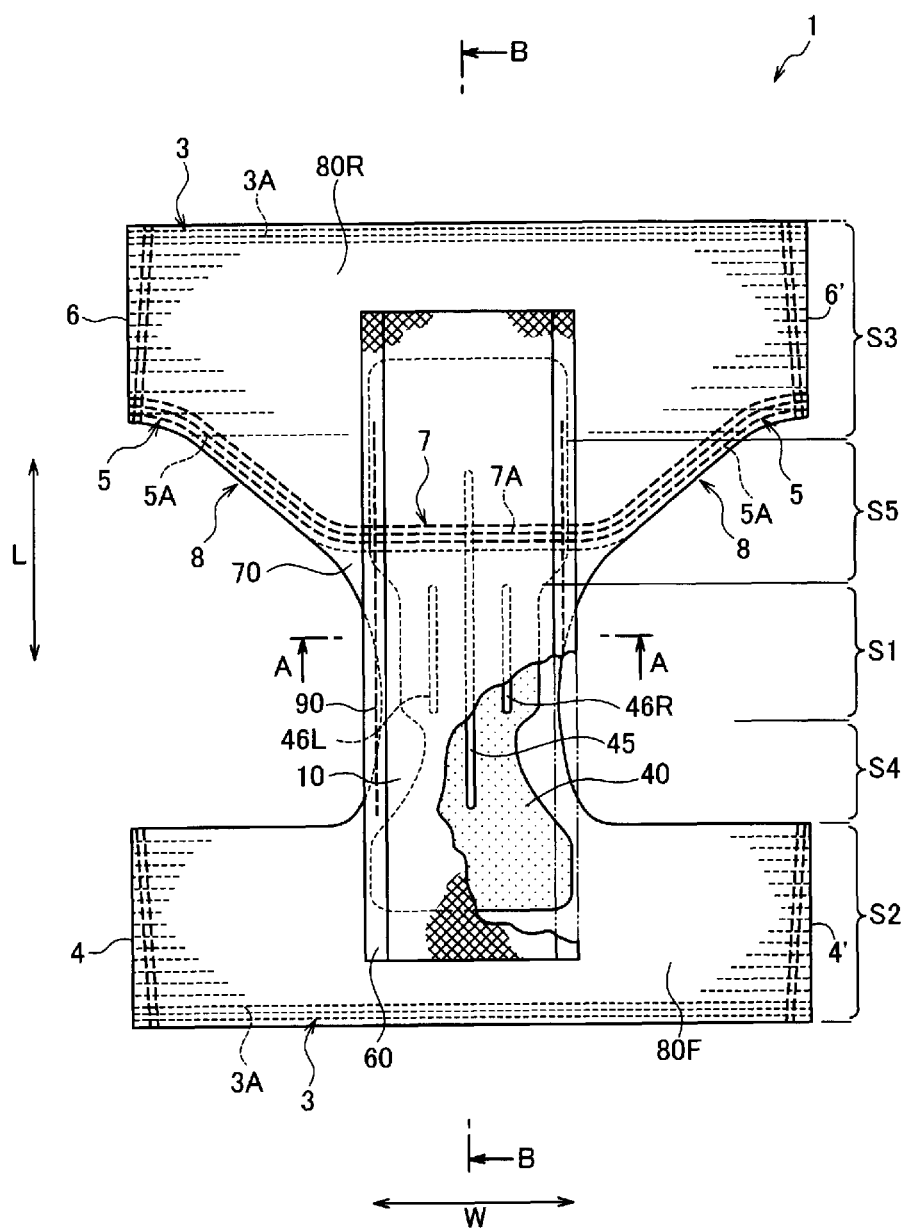
FIG. 2 is an exploded plan view of the diaper 1 according to the first embodiment.
Figure 3:
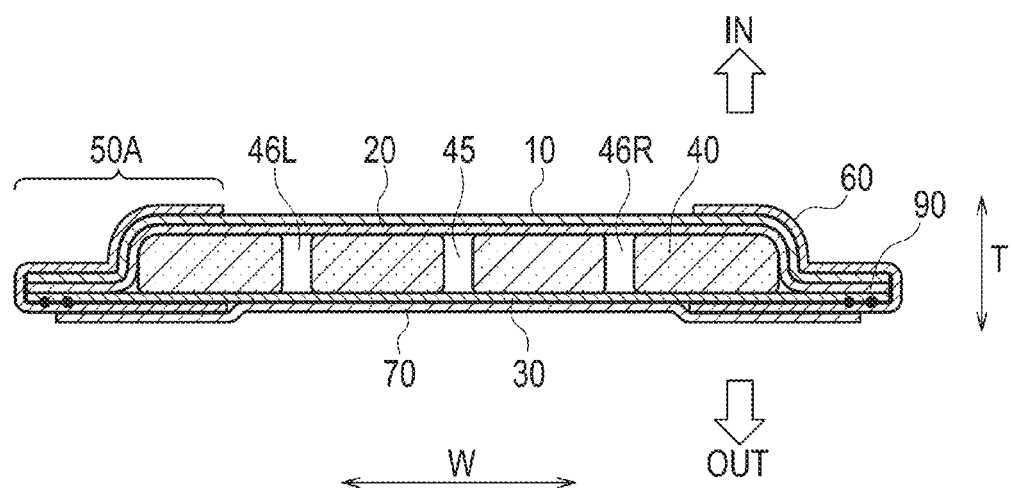
FIG. 3 is a widthwise sectional view of the diaper 1 taken along the line A-A shown in FIG. 2.
Figure 4:
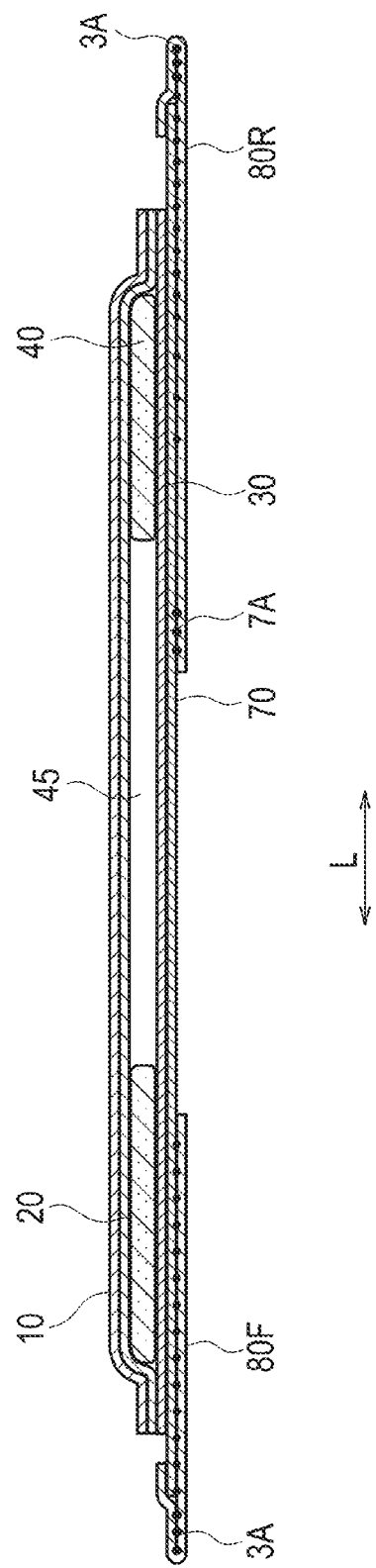
FIG. 4 is a lengthwise sectional view of the diaper 1 taken along the line B-B shown in FIG. 2.

FIG. 2 is an exploded plan view of the disposable diaper 1 according to the embodiment. FIG. 3 is a widthwise sectional view of the disposable diaper 1 taken along the line A-A shown in FIG. 2. FIG. 4 is a lengthwise sectional view of the disposable diaper 1 taken along the line B-B shown in FIG. 2.

As shown in FIG. 2 to FIG. 4, the disposable diaper 1 has: a front waistline region S2 which corresponds to a wearer's front waistline; and a back waistline region S3 which corresponds to the wearer's back waistline. The disposable diaper 1 also has a crotch portion region S1, a foreside middle inside leg region S4 and a backside middle inside leg region S5.

The crotch portion region S1 is a region applied to a wearer's crotch portion at which a width between both legs is the narrowest when the wearer closes his or her legs. The foreside middle inside leg region S4 is positioned between the crotch portion region Si and the front waistline region S2 in a lengthwise direction L of an absorber 40. The backside middle inside leg region S5 is positioned between the crotch portion region S1 and the back waistline region S3 in the lengthwise direction L.

The front waistline side edge portion 4 is bonded with the back waistline edge portion 6 and the front waistline edge portion 4' is bonded with a back waistline edge portion 6', whereby the disposable diaper 1 is formed as a pant-type diaper.

A waist gather 3 is provided in the front waistline region S2 and the back waistline region S3. The waist gather 3 has an elongated waist elastic member 3A, such as a synthetic rubber, which is disposed so as to expand or shrink along a widthwise direction W of the absorber 40. The waist elastic member 3A is bonded with an exterior topsheet 70, a foreside exterior backsheet 80F and a backside exterior backsheet 80R by means of an adhesive (for example, a hot-melt adhesive) in a state in which the member is expanded along the widthwise direction W of the disposable diaper 1.

A leg gather 5 and an absorber crossing gather 7 are formed at the middle inside leg edge portion 8 of the backside exterior backsheet 80R. The leg gather 5 is formed so as to be taken along a wearer's leg portion. The absorber crossing gather 7 is formed so as to cross the absorber 40 along the widthwise direction W. The leg gather 5 and the absorbent crossing gather 7 integrally communicate with each other. The leg gather 5 has a plurality of leg elastic members 5A, and the absorber crossing gather 7 has a plurality of crossing elastic members 7A which communicate with the leg elastic members 5A.

The disposable diaper 1 is provided with a topsheet 10, an absorber 40, a side sheet 60, an exterior topsheet 70, a foreside exterior backsheet 80F, and a backside exterior backsheet 80R. The topsheet 10, the absorber 40, the side sheet 60, the exterior topsheet 70, and the foreside exterior backsheets 80F and 80R are bonded with each other by means of an adhesive or thermal fusion bonding or the like.

The topsheet 10 is a sheet forming a skin contact surface which can come into direct contact with the wearer's skin. The topsheet 10 is formed of a liquid-permeable sheet such as a hydrophilic nonwoven cloth or a woven cloth, an aperture plastic film, or an aperture hydrophilic nonwoven cloth.

An absorber topside covering sheet 20 is provided between the topsheet 10 and the absorber 40. The absorber topside covering sheet 20 is formed of a liquid-permeable sheet such as a hydrophilic nonwoven cloth or a woven cloth, an aperture plastic film, an aperture hydrophobic nonwoven cloth, or tissue.

An absorber backside covering sheet 30 is provided at a non-skin contact surface side serving as a face opposite to the topsheet 10 or the absorbent topside covering sheet 20. The absorber backside covering sheet 30 is formed of a leakage-preventing sheet such as a liquid-impermeable film (for example, polyethylene). In FIG. 3, although not shown, the absorber topside covering sheet 20 is bonded with the absorber backside covering sheet 30 at a portion at which slits (central slit 45 and side slits 46L, 46R) are formed.

The absorber 40 is covered with the absorber topside covering sheet 20 and the absorber backside covering sheet 30. The absorber 40 has: a lengthwise direction L which is oriented from the front waistline region S2 to the back waistline region S3; and a widthwise direction which is orthogonal to the lengthwise direction L. Further, the absorber 40 has: an inward direction IN which is oriented to a wearer wearing the disposable diaper 1 and an outward direction OUT which is oriented to be opposite to the inward direction.

At a side edge portion 50A at which the absorber topside covering sheet 20 and the absorber backside covering sheet 30 overlap each other at the outside of the widthwise direction W of the absorber 40, a side elastic member 90 is provided in a state in which the member expands along the lengthwise direction L. The side elastic member 90 is continuous from the foreside middle inside leg region S4 to the backside middle inside leg region S5 through the crotch portion region S1. The side elastic member is provided between the absorber backside covering sheet 30 and a side sheet 60. The side elastic member 90 is formed of a synthetic rubber having elasticity.

The side sheet 60 is provided so as to integrally cover the topsheet 10, the absorber topside covering sheet 20, and the absorber backside covering sheet 30 at both side edges in the widthwise direction W of the absorber 40. The side sheet 60 is formed of a sheet such as a liquid-impermeable nonwoven cloth, and a leakage-preventing wall for preventing side leakage of bodily waste is comprised of the side sheet 60 and the side elastic member 90.

The exterior topsheet 70 is formed from the front waistline region S2 to the back waistline region S3 through the foreside middle inside leg region S4, the crotch portion region S1, and the backside middle inside leg region S5. The exterior topsheet 70 is formed so that its width in the widthwise direction W is greater in the front waistline region S2 and the back waistline region S3 than in any other region. The exterior topsheet 70 can be formed of an air-through nonwoven cloth, a spun bond nonwoven cloth, an SMS nonwoven cloth, or a water-resistive film or the like.

The foreside exterior backsheet 80F is provided at a non-skin contact surface side more than the exterior topsheet 70 in the front waistline region S2. The backside exterior backsheet 80R is provided at the non-skin contact surface side more than the exterior topsheet 70 in the back waistline region S3. One end of the foreside exterior topsheet 80F in the lengthwise direction L and one side of the backside exterior backsheet 80R in the lengthwise direction is folded back to the skin contact surface side, so as to envelop the end parts in the lengthwise direction L of the exterior topsheet 70. The foreside exterior backsheet 80F can be formed of an air-through nonwoven cloth, a spun bond nonwoven cloth, an SMS nonwoven cloth, or a water-resistive film or the like.

Materials described in Japanese Patent Application Laid-open No. 2006-346439, for example, may be employed for constituent elements constituting the abovementioned disposable diaper 1.

(2) Structure of an Absorber

Figure 5:
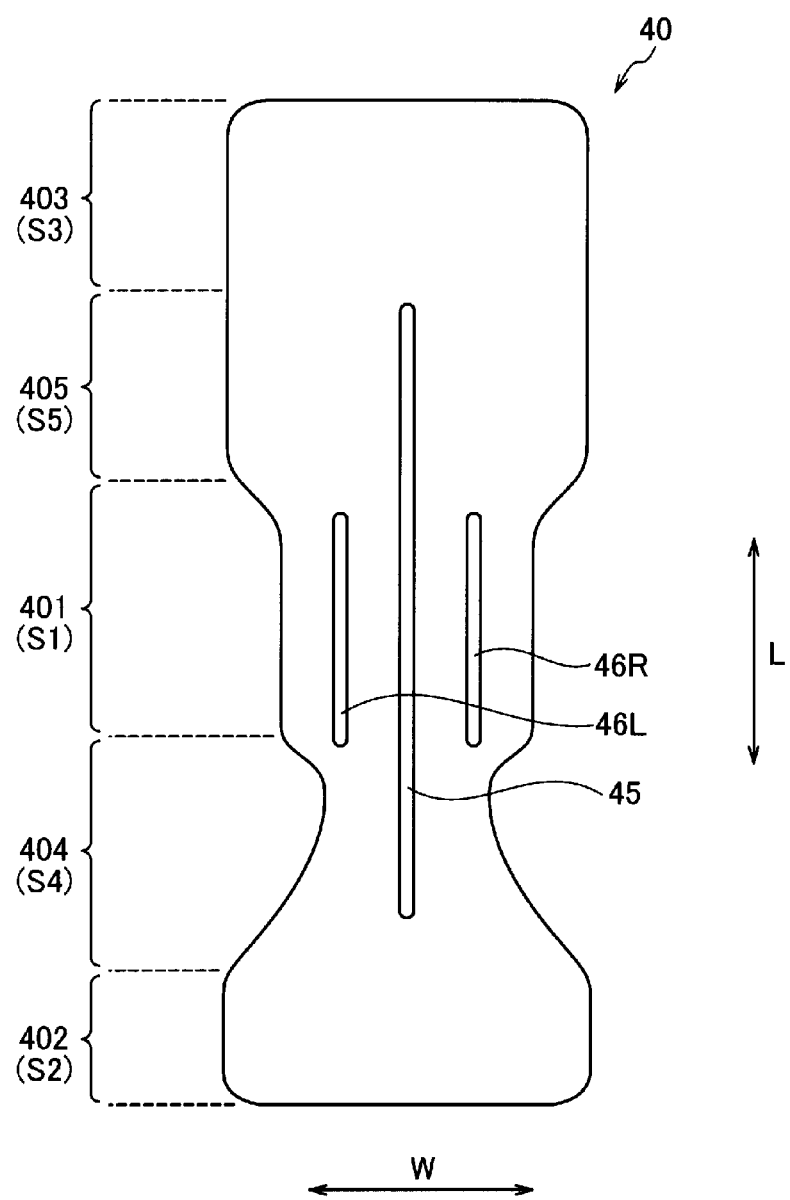
FIG. 5 is a plan view of an absorber 40 according to the first embodiment.

FIG. 5 is a plan view of an absorber 40. As shown in FIG. 5, the absorber 40 has a central inside leg portion 401, a front waistline portion 402, a back waistline portion 403, a front middle inside leg portion 404, and a back middle inside leg portion 405.

In the embodiment, a width of a narrowed portion of the front middle inside leg portion 404 which corresponds to the foreside middle crotch portion S4 is the narrowest. The second narrowest portion is a width of the central inside leg portion 401 positioned in the crotch portion region S1 (see FIG. 1).

It should be appreciated that the absorber is not limited to the depicted shape, the absorber may take other forms, as will be readily appreciated by those skilled in the art.

In the embodiment, the absorber 40 is employed as the one in which a water absorbent polymer is incorporated into a cotton-like pulp of 200 g/m². In addition, a central slit 45 and a side slit 46L, side slit 46R are formed at the absorber 40 as described above.

The central slit 45 is formed at the absorber 40 along the lengthwise direction L, namely so that the absorber 40 can be curved to a wearer so as to be convex in the inward direction IN. In the embodiment, the central slit 45 comprises a central curve forming portion. The side slit 46L, the side slit 46R are formed at the absorber 40 along the lengthwise direction L, namely so that the absorber 40 can be curved to be convex in the outer direction OUT either side of the central slit 45. In the embodiment, the side slit 46L, the side slit 46R comprise side curve forming portions.

A width of the central slit 45 is preferably about 10 mm, and a length thereof is preferably about 200 mm. The width of the side slit 46L, side slit 46R is preferably about 10 mm and a length thereof is preferably about 120 mm. In addition, the thickness of the absorber 40 is preferably about 2.0 mm.

Figure 6:
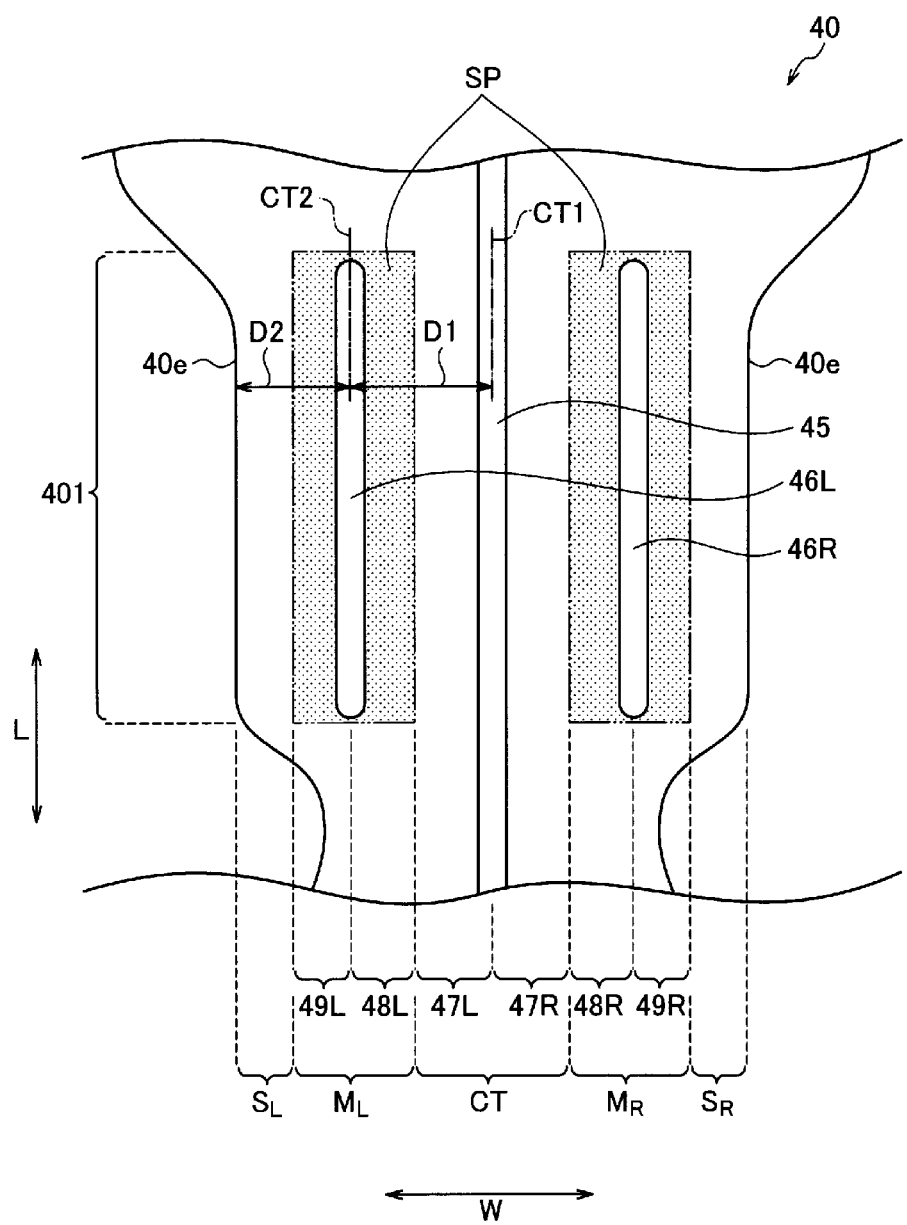
FIG. 6 is a partially enlarged plan view of the absorber 40 according to the first embodiment.

FIG. 6 is a partially enlarged plan view of the absorber 40. As shown in FIG. 6, the absorber 40 has a central portion CT formed at a central part of the absorber 40 in the widthwise direction W. In addition, the absorber 40 has a pair of side edge portions $S_L$, $S_R$ formed at a side edge 40e of the absorber 40 in the widthwise direction W. Further, this absorber has a pair of middle portions $M_L$, $M_R$ positioned between the central portion and the side edge portions. The central portion CT, the middle portion $M_L$, the middle portion $M_R$, the side edge portion $S_L$, and the side edge portion $S_R$ are formed at least in a crotch portion region S1 (central inside leg portion 401).

The central portion CT includes a sub-central portion 47L and a sub-central portion 47R which are regions from the boundaries associated with the middle portion $M_L$ and the middle portion $M_R$ respectively to the central slit 45 in the widthwise direction W.

The middle portions $M_L$, $M_R$ each include an inside middle portion 48L, 48R, which is a region from the respective side slit 46L, 46R to a boundary associated with the central portion CT in the widthwise direction. In addition, each middle portion $M_L$, $M_R$ includes an outside middle portion 49L, 49R which is a region from a respective one of the side slits 46L, 46R to a boundary associated with a respective one of the side edge portions $S_L$, $S_R$ in the widthwise direction W.

The central portion CT is deformed so that the absorber 40 is curved at a portion of the central slit CT to be convex toward a wearer. The middle portions $M_L$, $M_R$ including the side slits 46L, 46R are deformed at a side opposite to the central portion CT, namely so as to be convex at the non-skin contact surface side. Specifically, the central portion CT is convex toward the wearer in a state in which it is sandwiched between the wearer's legs, whereas the side edge portions $S_L$, $S_R$ rise to the wearer's side by shrinkage of the side elastic member 90. The middle portions $M_L$, $M_R$ are folded at a portion of the respective side slits 46L, 46R, and are convex at a side opposite to the central portion CT.

The middle portions $M_L$, $M_R$ are formed from positions which correspond to half of a distance D1 between a center CT1 of the central slit 45 and a center CT2 of the respective side slit 46L, 46R to a position which corresponds to half of a distance D2 between the respective side slit 46L, 46R and a respective side edge 40e of the absorber 40. In the embodiment, the distance D1 is preferably set to about 40 mm and the distance D2 is preferably set to about 35 mm. In addition, in the widthwise direction W, the width of the sub-central portions 47L, 47R is substantially identical to that of the side edge portions $S_L$, $S_R$.

An average basis weight of a water absorbent polymer at the central portion CT and the side edge portion $S_L$, the side edge portion $S_R$ is preferably 90 g/m². On the other hand, an average basis weight of a water absorbent polymer at the middle portion $M_L$, the middle portion $M_R$ is preferably 240 g/m². That is, the average basis weight of the water absorbent polymer at the central portion CT and the side edge portion $S_L$, the side edge portion $S_R$ is smaller than that of the water absorbent polymer at the middle portion $M_L$, the middle portion $M_R$.

The average basis weight of the water absorbent polymer is a mass of the water absorbent polymer incorporated per a unit area of the portion, and even if a basis weight is different in the portion (for example, middle portion $M_L$, such basis weight is defined as a value obtained by averaging the mass of the water absorbent polymer incorporated in an area of the portion by a unit area. The central slit 45 and the side slits 46L, 46R are not incorporated in computation of an average basis weight, since neither a pulp nor a water absorbent polymer exists.

A high basis weight portion SP at which the average basis weight of the water absorbent polymer at the middle portions $M_L$, $M_R$ is 240 g/m² is formed around the side slits 46L, 46R. For example, a water absorbent polymer having properties of water absorption magnification of 64 g/g, water retention magnification of 40 g/g, and absorption velocity (Vortex approach) of 29 seconds can be employed.

A testing method using the Vortex approach is generally as follows. First, sodium chloride of 27.0 g (reagent: grade 1) and ion exchange water are added to hydrochloride water solution (reagent: grade 1) to make a solution of 3,000.0 g and then the resultant solution is stirred until it is dissolved. In addition, a testing liquid of 1 liter of the solution above is put into a beaker; a temperature of the testing liquid is adjusted to 25 degrees Centigrade+−1 degree Centigrade; and a testing liquid of 50 g is transferred to a beaker of 100 ml. The beaker is placed on a magnetic stirrer (MITAMURA RIKEN KOGYO INC. MAGMIX STIRRER), and is stirred at 600 rotations per minute. The number of rotations is adjusted to 600+−30 rotations per minute.

Next, a water absorbent polymer (SAP) of 2.00 g is entered into the beaker, and time is measured until a liquid surface becomes smooth. A judgment as to whether or not the liquid surface becomes smooth is based on the fact that an inclination of whirl of the liquid that is severely rotating is close to a plane, and is made by observing whether illumination reflected on the liquid surface of the whirl goes up or out.

It is preferable that the average basis weight of the water absorbent polymer at the central portion CT and side edge portions $S_L$, $S_R$ is 0 g/m² or more and 300 g/m² or less, and it is more preferable that the weight is 0 g/m² or more and 90 g/m² or less. In addition, it is preferable that the average basis weight of the water absorbent polymer at the middle portion $M_L$ (middle portion $M_R$) is 100 g/m² or more and 600 g/m² or less and it is more preferable that the weight is 100 g/m² or more and 400 g/m² or less. However, the average basis weight of the water absorbent polymer at the central portion CT and the side edge portions $S_L$, $S_R$ is less than that of the water absorbent polymer at the middle portions $M_L$, $M_R$.

In addition, it is preferable that the average basis weight of the water absorbent polymer at the sub-central portions 47L, 47R is less than that of the water absorbent polymer at the inside middle portions 48L, 48R. Further, it is preferable that the average basis weight of the water absorbent polymer at the side edge portions $S_L$, $S_R$ is less than that of the water absorbent polymer at the outside middle portions 49L, 49R.

(3) Shape Change of an Absorber

Figure 7:
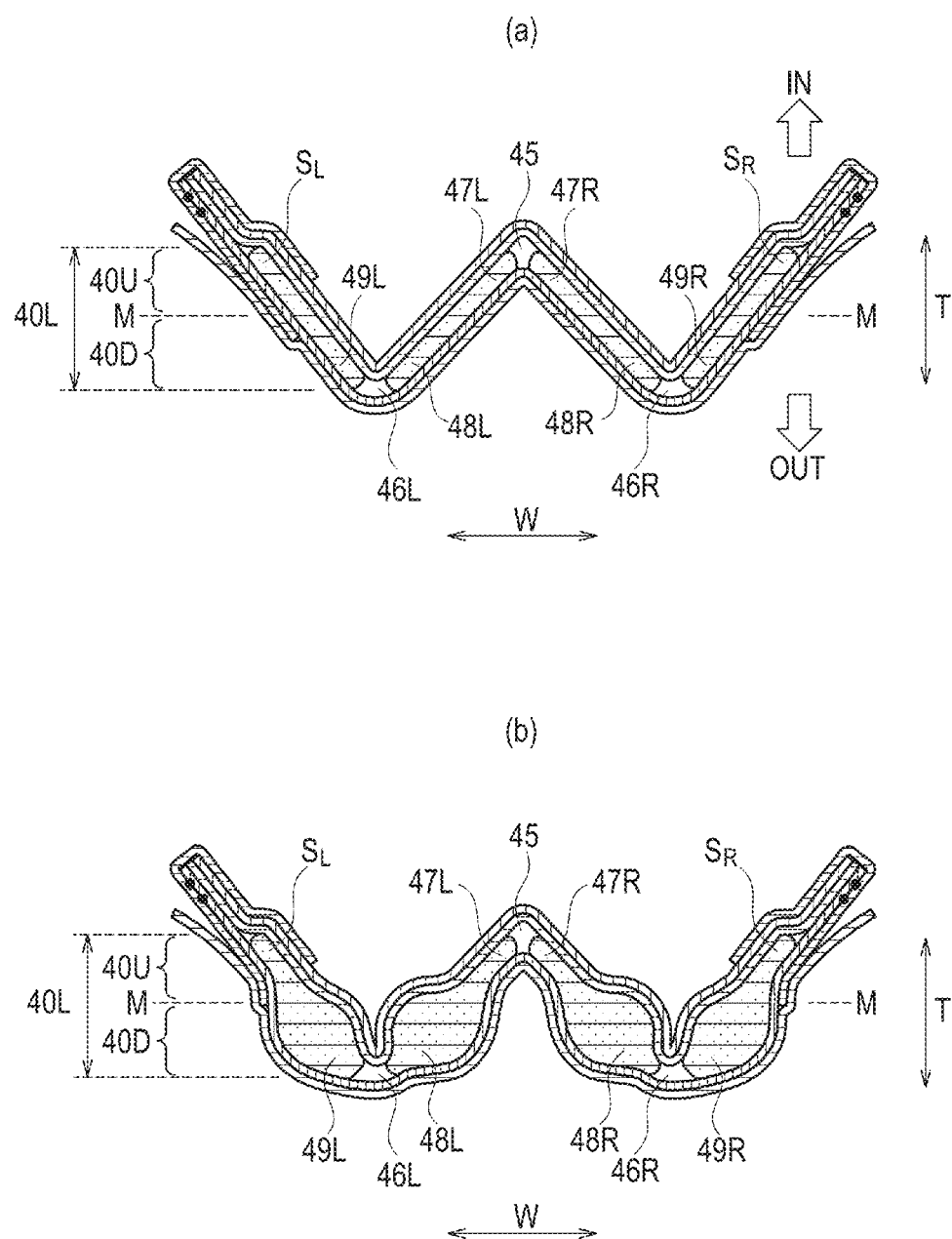
FIG. 7(a) is a sectional view schematically showing a wearing state of a disposable diaper 1 while the absorber 40 according to the first embodiment does not absorb bodily waste.
FIG. 7(b) is a sectional view schematically showing a wearing state of the disposable diaper 1 while the absorber 40 absorbs bodily waste.

FIG. 7(a) is a sectional view (which is taken along the line A-A of FIG. 2) schematically showing a state in which the absorber 40 has not absorbed bodily waste, and FIG. 7(b) is a sectional view (which is taken along the line A-A of FIG. 2) schematically showing a wearing state of the disposable diaper 1 in a state in which the absorber 40 absorbs bodily waste.

As shown in FIG. 7(a), when the disposable diaper 1 is worn, the absorber 40 is curved with respect to the central slit 45 and the side slits 46L, 46R, and the cross-sectional shape that is taken along the widthwise direction W of the disposable diaper 1 is deformed at the W-letter shape. As a result, a sub-central portion 47L, a sub-central portion 47R, a side edge portion $S_L$, and a side edge portion $S_R$ are positioned at an upper area 40U which is proximal to a wearer's body above an imaginary line M obtained by dividing a height 40L of the deformed absorber 40 into two sections. On the other hand, in an elevation direction T, inside middle portions 48L, 40R and outside middle portions 40L, 40R are positioned in a lower area 40D which is distant from the wearer's body and below the imaginary line M.

FIG. 7(b) shows a wearing state of the disposable diaper 1 in a state in which the absorber 40 absorbs bodily waste. As shown in FIG. 7(b), when the absorber 40 absorbs a predetermined amount of liquid such as urine, the inside middle portions 48L, 48R and outside middle portions 49L, 49R of which average basis weight of the water absorbent polymer is large swell more than the sub-central portion 47L, sub-central portion 47R and the side edge portions $S_L$. $S_R$ of which average basis weight of the water absorbent polymer is small. Thus, in a case where the absorber 40 absorbs a predetermined amount of liquid, a total thickness of the absorber 40 in the central portion CT and side edge portions $S_L$, $S_R$ becomes smaller than that of the absorber 40 in the inside middle portions 48L, 48R and the outside middle portion 49L, 49R.

Figure 8:
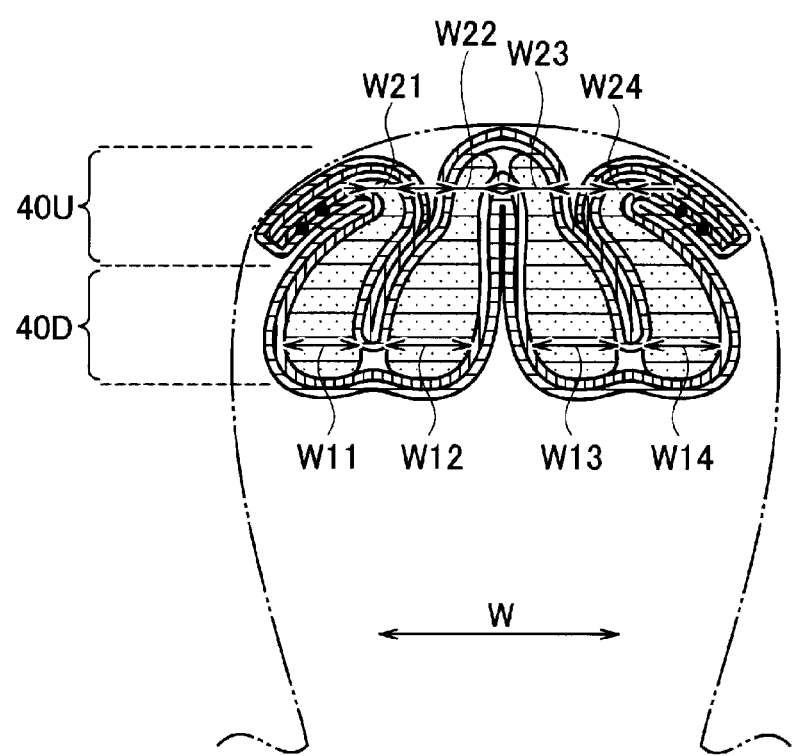
FIG. 8 is a sectional view (at the time of closing legs) schematically showing a wearing state of the disposable diaper 1 in which the absorber 40 according to the first embodiment absorbs bodily waste.

FIG. 8 is a sectional view schematically showing a wearing state of the disposable diaper 1 in a state in which the absorber absorbs bodily waste, specifically a case in which a wearer closes his or her legs. The imaginary line in the figure indicates the wearer's crotch portion and both leg portions.

As shown in FIG. 8, if the wearer closes his or her legs in a state in which the absorber 40 absorbs bodily waste, the cross-sectional shape of the disposable diaper 1 varies from the state shown in FIG. 7(b) to the state shown in FIG. 8. At this time, the thickness of the absorber 40 in the upper region 40U (a total thickness of W21 to W24 in the figure), in which an expansion rate after absorption of liquid (about 500 cc) is lower, is about 18 mm. Specifically, the thickness before liquid absorption is about 2.0 mm in a region in which the average basis weight of the water absorbent polymer is 90 g/m², whereas the thickness after liquid absorption is about 4.5 mm. Namely, the thicknesses W21 to W24 of the sub-central portion 47L, sub-central portion 47R and the side edge portions $S_R$, $S_L$ are about 4.5 mm, respectively. The thicknesses W21 to W24 are a thickness of the absorber 40 at a position which is lowered by a distance of ⅓ of the upper region 40U from an upper end of the upper region 40U in the elevation direction T.

On the other hand, the thickness of the absorber 40 in the lower region 40D (a total thickness of W11 to W14 in the figure) is larger than that of the absorber 40 in the upper region 40U. Thus, the cross-sectional shape that is taken along the widthwise direction W of the absorber 40 (disposable diaper 1) is formed in a tapered shape toward the wearer's crotch portion. The thicknesses W11 to W14 are a thickness of the absorber 40 at a position rising by a distance of ⅓ of the lower region 40D from a lower end of the lower region 40D in the elevation direction T.

In a case where the absorber 40 absorbs a predetermined amount of liquid (about 500 cc), it is preferable that the thickness of a high basis weight portion SP (the thickness of the disposable diaper 1 at the positions of W11 to W14 of FIG. 8) in a state in which the absorber 40 is curved is 20 mm or more and 120 mm or less, it is more preferable that the thickness is 20 mm or more and 80 mm or less, and it is further preferable that the thickness is 20 mm or more and 40 mm or less. In addition, it is preferable that the thickness of a portion other than the high basis weight portion SP (the thickness of the disposable diaper 1 at the positions of W21 to S24 of FIG.

8) in a state in which the absorber 40 is curved is low, preferably 4 mm or more and 20 mm or less. In a case where the thicknesses WI 1 to W14 of the lower region 40D are increased, the higher the central portion CT taken along the elevation direction T is, namely, the wider the central portion CT prior to deforming the absorber 40 is, the more easily the central portion CT enters the wearer's crotch portion.

The disposable diaper 1 described hereinbefore is provided with: the central slit 45 formed at the absorber 40 so that the absorber 40 can be curved to be convex toward a wearer; and a pair of side slits 46L, 46R which are formed at the absorber 40 so that the absorber 40 can be curved to be convex so as to be oriented to a side opposite to the central slit 45. Thus, at the time of wearing the disposable diaper 1, the central portion CT that is formed to be convex toward the wearer's excretion portion easily comes into intimate contact with the excretion portion. In addition, the middle portion $M_L$ and the middle portion $M_R$ each form a concave portion, so that bodily waste easily enters the concave portion, and direct contact between the wearer's skin and bodily waste can be restrained.

Further, the average basis weight (90 g/m²) of the water absorbent polymer at the central portion CT and the side edge portions SL, SR is less than the average basis weight (240 g/m²) of the water absorbent polymer at the middle portions $M_L$, $M_R$. Specifically, the average basis weight of the water absorbent polymer at the sub-central portions 47L, 47R is less than that of the water absorbent polymer at the inside middle portions 48L, 48R; and the average basis weight of the water absorbent polymer at the side edge portions $S_L$, $S_R$ is less than that of the water absorbent polymer at the outside middle portions 49L, 49R.

Therefore, after the absorber 40 absorbs a predetermined amount of liquid, the thickness of the central portion CT and the side edge portions $S_L$, $S_R$, which have a low average basis weight of the water absorbent polymer, is (smaller than that of the middle portion $M_L$ and the middle portion $M_R$ in which the average basis weight is large.

Thus, the central portion CT, which is proximal to the wearer's crotch portion, and the side edge portions $S_L$, $S_R$ are restrained in thickness after liquid absorption, the wearer hardly has an uncomfortable feeling, and it is ensured that the absorber comes into intimate contact with the excretion portion. In addition, at the middle portion $M_L$ and the middle portion $M_R$, each of which is distant from the wearer's crotch portion, the average basis weight of the water absorbent polymer is large, so that absorptive power can be improved without the wearer having an uncomfortable feeling. In particular, after bodily waste such as urine has been absorbed a plurality of times, such a shape can be maintained to prevent the wearer from having an uncomfortable feeling or leakage of bodily waste.

In the embodiment, the middle portions $M_L$, $M_R$ are formed, in the widthwise direction W, from a position which corresponds to half of the distance D1 between a center CT1 of the central slit 45 and a center CT2 of the side slit 46L (or the side slit 46R) to a position which corresponds to half of the distance D2 between the side slit 46L (or the side slit 46R) and the side edge 40e of the absorber 40. In addition, the width of the sub-central portions 47L, 47R is substantially identical to that of the side edge portions $S_L$, $S_R$. Thus, as shown in FIG. 7(a) and FIG. 7(b), among the upper region 40U and the lower region 40D that are obtained by dividing the curved absorber 40 into two sections, the central portion CT and the side edge portions $S_L$, $S_R$ can be disposed, in the elevation direction T, in the upper region 40U that is proximal to the wearer's crotch portion; and the middle portions $M_L$, $M_R$ can be disposed in the lower region 40D that is distant from the wearer's inside leg portion. Namely, the thickness of the absorber 40 in the upper region 40U is restrained, and an uncomfortable feeling of the wearer or leakage of bodily waste can be reliably prevented.

In the embodiment, the absorber topside covering sheet 20 is bonded with the absorber backside covering sheet 30 at a portion at which slits (central slit 45 and side slits 46L, 46R) are formed. Thus, deformation of the absorber 40 causing a slit portion to close or twisting of the absorber 40 from a slit portion can be restrained. In addition, even in a case where the absorber 40 absorbs liquid and swells, closing of a slit portion can be restrained. Therefore, a slit portion can easily function as a curve forming portion reliably.

(4) First Modification

Figure 9:
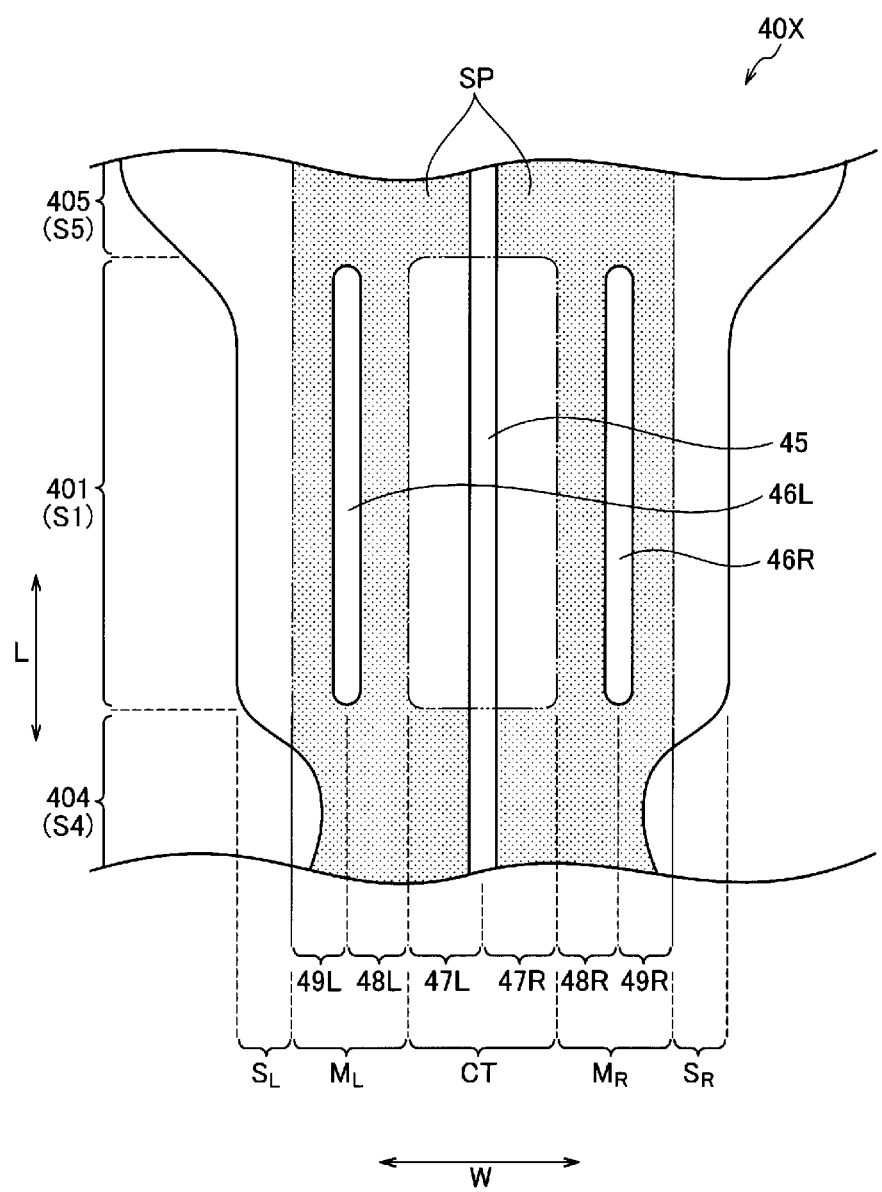
FIG. 9 is a partially enlarged plan view of the disposable diaper 1 according to a modification of the first embodiment.

FIG. 9 is a partially enlarged plan view of an absorber 40X according to a modification of the embodiment. As shown in FIG. 9, in the absorber 40X, in a lengthwise direction L, an average basis weight of a water absorbent polymer in a region positioned at an outside of the central portion CT is more than that of a water absorbent polymer at the central portion CT.

Specifically, an average basis weight of a water absorbent polymer at the foreside middle inside leg region S4, which is a portion close to the front waistline region S2 and adjacent to a central inside leg portion 401 (crotch portion region S1), and at the backside middle inside leg region S5, which is a portion close to a back waistline region S3 and adjacent to the crotch portion region S1, is more than that of a water absorbent polymer at the central portion CT positioned in the crotch portion region S1. For example, a basis weight of the portions can be set to 240 g/m² like the middle portions $M_L$, $M_R$.

Namely, in the absorber 40X, the longitudinal and transverse extending peripheries of a sub-central portion 47L and a sub-central portion 47R of the portion of the central portion CT extending the length of crotch region S1 are surrounded by an area in which an average basis weight of a water absorbent polymer is large. An outside region, in the lengthwise direction L, of the central portion CT, that is the region that lies outside the crotch portion S1, is hardly deformed if the absorber absorbs liquid and swells greatly, and thus, W-letter shaped deformation at the central inside leg portion 401 of the absorber 40X does not have an influence on the region, and the region is easily maintained to be planar. In addition, an outside region, in the lengthwise direction L, beyond the crotch portion region S1 is not sandwiched by a wearer's crotch portion, so that an average to basis weight of the water absorbent polymer of this portion is increased, whereby absorptive power can be improved without increasing an uncomfortable feeling at the crotch portion.

(5) Second Modification

Figure 10:
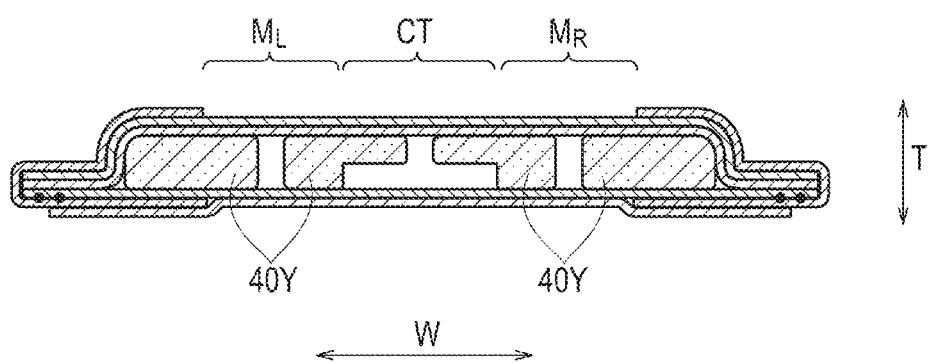
FIG. 10 is a sectional view of the disposable diaper 1 according to a modification of the first embodiment.
Figure 11:
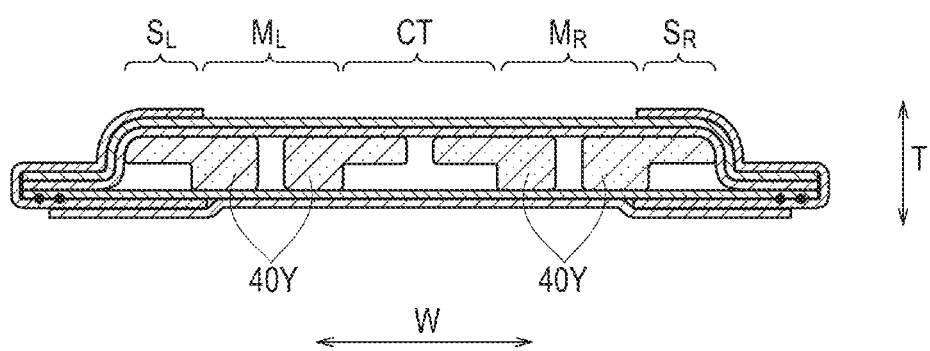
FIG. 11 is a sectional view of the disposable diaper 1 according to a modification of the first embodiment.

FIG. 10 and FIG. 11 are sectional views (which is taken along the line A-A of FIG. 2) of a disposable diaper 1 including an absorber 40Y and an absorber 40Y' according to the modification of the embodiment. As shown in FIG. 10 and FIG. 11, a thickness of an absorber at any of at least a central portion CT and a side edge portion $S_L$ and a side edge portion $S_R$ is smaller than that of an absorber at a middle portion $M_L$ and a middle portion $M_R$. The reduced thickness portions may extend for the length of the crotch portion region S1 only.

According to the absorbent 40Y and the absorbent 40Y', the absorber 40Y (absorber 40Y') may adopt the state shown in FIG. 8 before the absorber absorbs liquid. Thus, absorptive power of the disposable diaper 1 is improved, whereas a feeling of wearing before liquid absorption can also be improved.

The thickness of the side edge portion $S_L$ and the side edge portion $S_R$ may be increased like the middle portion $M_L$ and the middle portion $M_R$, like the absorber 40Y, as shown in FIG. 10, so that the side edge portions have the same thickness as the middle portions, or alternatively, may be decreased like the central portion CT as in the absorber 40Y', as shown in FIG. 11, where the thickness of the side edge portions is equal to the thickness of the central portion, wherein in both cases the thickness of the central portion is less than the thickness of the middle portions.

Second Embodiment

Figure 12:
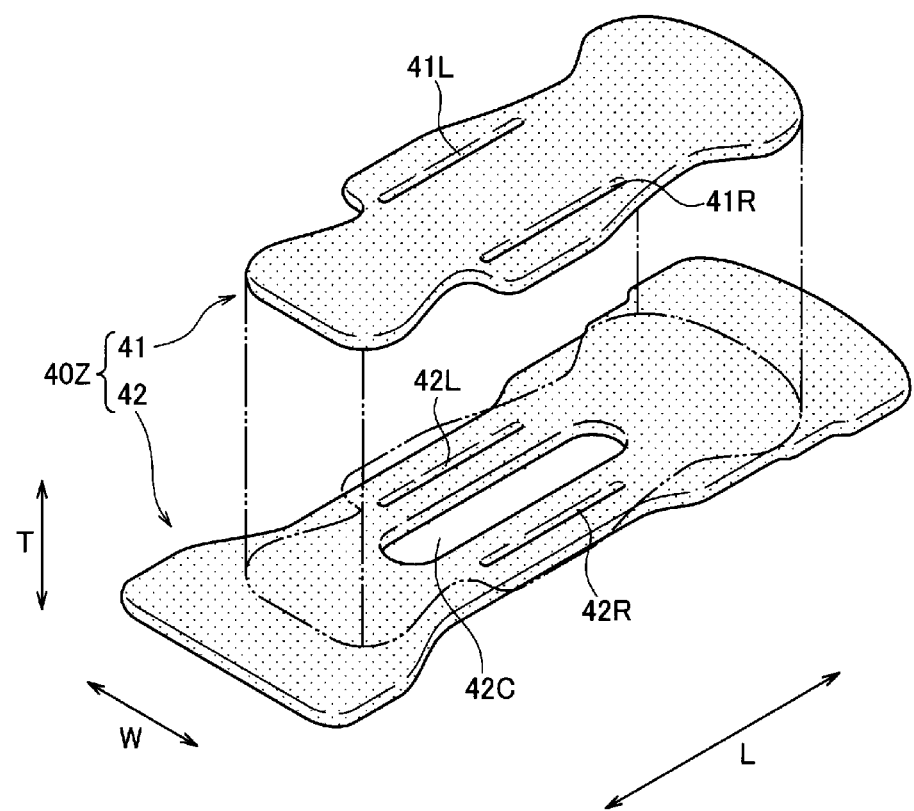
FIG. 12 is a perspective view of a simple absorber 40Z according to a second embodiment.
Figure 13:
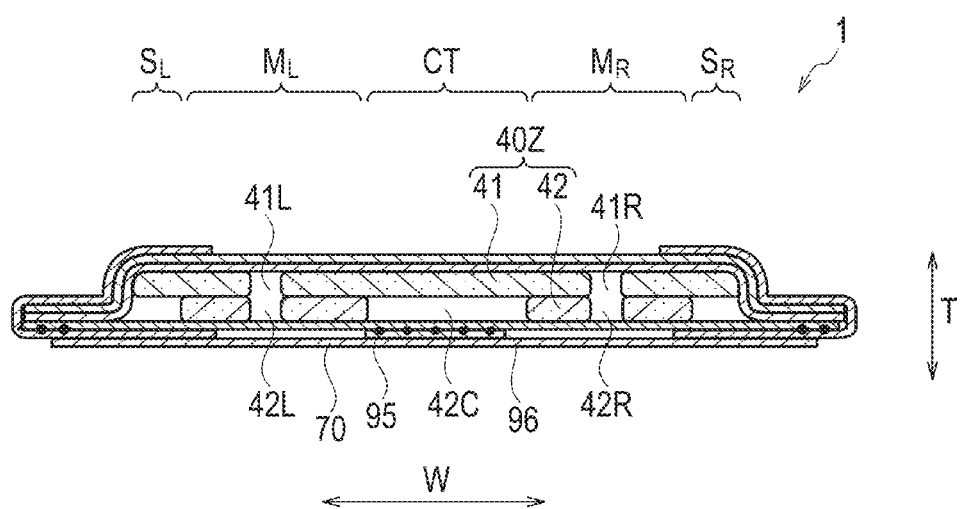
FIG. 13 is a sectional view of a disposable diaper 1 according to the second embodiment.

FIG. 12 is a perspective view of a simple absorber 40Z according to a second embodiment. FIG. 13 is a sectional view (which is taken along the line A-A of FIG. 2) of a disposable diaper 1 including an absorber 40Z. As shown in FIG. 12 and FIG. 13, an absorber 40Z according to the embodiment is a two-layer structure.

Specifically, the absorber 40Z has a first layer 41 and a second layer 42 which are superimposed on one another. The first layer 41 is positioned at a skin contact surface side with a wearer, and the second layer 42 is positioned at a non-skin contact surface side of the wearer. Side slits 41L, 41R extending along a lengthwise direction L are formed at the first layer 41. The side slits 41L, 41R are formed at a crotch portion region S1 (central inside leg portion 401) like side slits 46L, 46R.

In the second layer, a central aperture 42C extending along the lengthwise direction L is formed and side slits 42L, 42R are also formed. The central aperture 42C and the side slits 42F, 42R are formed at a crotch portion region S1 (central inside leg portion 401) like the central slit 45 or the like. A width of the central aperture 42C is preferably about 40 mm, and the side slits 41L, 41R and the side slits 42L, 42R are preferably about 10 mm wide.

In the case of the absorber 40Z, as shown in FIG. 13, the central portion CT is formed of only the first layer 41, the side edge portions $S_L$, $S_R$ are formed only of the first layer 41, and a middle portion $M_L$ and a middle portion $M_R$ are formed of the first layer 41 and the second layer 42. In addition, an average basis weight of a water absorbent polymer in the first layer 41 is preferably 90 g/m². An average basis weight of a water absorbent polymer in the second layer 42 is preferably 150 g/m². Thus, as in the first embodiment, an average basis weight of a water absorbent polymer at the central portion CT and the side edge portion $S_L$, the side edge portion $S_R$ is preferably 90 g/m², and an average basis weight of a water absorbent polymer at the middle portion $M_L$, the middle portion $M_R$ is preferably 240 g/m².

In addition, in the disposable diaper 1, including the absorber according to the embodiment, a central elastic member 95 (central curve forming portion) is provided between an absorber backside covering sheet 30 and an elastic member covering sheet 96. The central elastic member 95 is provided as a plurality of elastic strands along the lengthwise direction L to thereby deform the absorber 40Z so that the central portion CT becomes convex toward a wearer. Thus, in the disposable diaper 1 according to the embodiment, unlike the central slit 45 (see FIG. 3), a slit penetrating in the elevation direction T is not formed. It should be noted that the central elastic member is not limited to a plurality of elastic strands but may take other forms as will be readily appreciated by those skilled in the art.

With the second layer 42 being positioned at a skin contact surface with a wearer, the first layer may be positioned at the wearer's non-skin contact surface side. According to the disposable diaper 1 according to the embodiment, since there is employed the absorber 40Z in which the first layer 41 and the second layer 42 are superimposed on each other, an absorber of which thickness is different depending on a portion can be easily manufactured in comparison with a case in which an absorber of a one-layer structure is employed.

Other Embodiments

As described above, while the contents of the present invention have been disclosed through the embodiments of the present invention, it should not be understood that the statements and drawings forming part of the disclosure limit the present invention. From this disclosure, a variety of alternative embodiments, examples, and operational techniques would be self-evident to one skilled in the art.

For example, while, the absorber of the first and second embodiments has been described in combination with a pant-type disposable diaper 1, the absorber of the present invention may be applied to numerous other absorbent wearing articles, including but not limited to an open-type disposable diaper or a sanitary napkin.

While, in the first embodiment described above, the middle portions $M_L$, $M_R$ were formed from positions corresponding to half of the distance D1 between the center CT1 of the central slit 45 and the center CT2 of the respective side slit 46L, 46R to a position which corresponds to half of the distance D2 between the side slit 46L, 46R and the respective side edge 40e of the absorber 40, the middle portions $M_L$, $M_R$ may not always be formed at such a range. For example, a total width of the middle portions $M_L$, $M_R$ may be smaller than the width of the central portion CT.

While, in the first embodiment described above, the average basis weight (90 g/m²) of the water absorbent polymer at the central portion CT and the side edge portions $S_L$, $S_R$ was smaller than the average basis weight (240 g/m²) of the water absorbent polymer at the middle portions $M_L$, $M_R$, for example, the basis weight of the water absorbent polymer at the side edge portions $S_L$, $S_R$ may be identical to that of the water absorbent polymer at the middle portions $M_L$, $M_R$. In addition, the basis weight of the side edge portions $S_L$ and $S_R$, the middle portions $M_L$ and $M_R$, the sub-central portions 47L and 47R may not always be identical to each other. For example, if the average basis weight of the side edge portion $S_L$ is 90 g/m² and the average basis weight of the side edge portion $S_R$ is 100 g/m², the average basis weight of the entire side edge portion $S_L$, the side edge portion $S_R$ is 95 g/m².

While, in the first embodiment described above, the average basis weight (90 g/m²) of the water absorbent polymer at the central portion CT and the side edge portions $S_L$, $S_R$ was smaller than the average basis weight (240 g/m²) of the water absorbent polymer at the middle portion $M_L$, with the average basis weight of each portion being identical, a water absorption magnification of the water absorbent polymer at the central portion CT and the side edge portions $S_L$, $S_R$ may be smaller than that of the water absorbent polymer at the middle portions $M_L$, $M_R$. For example, while the water absorption magnification of the water absorbent polymer at the central portion CT and the side edge portions $S_L$, $S_R$ is on the order of 40 g/g, the water absorption magnification of the water absorbent polymer at the middle portions $M_L$, t $M_R$ may be on the order of 60 g/g. By disposition of such a water absorbent polymer as well, an advantageous effect similar to that of the above-described absorber can be attained.

While, in the first and second embodiments described above, a central curve forming portion was formed by employing slits or elastic members, the central curve forming portion may be formed by other means, such as but not limited to reducing the thickness of an absorber or applying emboss processing to the absorber.

Of course, the present invention includes a variety of embodiments which are not described herein. Therefore, a technical scope of the present invention is defined merely by specific matters of the invention according to a scope of claims which is reasonable from the above description.

The first aspect of the present invention described above may be arranged in at least the following items:

An absorber having a lengthwise direction; a widthwise direction which is orthogonal to the lengthwise direction; an inward direction which is oriented to a wearer; and an outer direction which is oriented to a side opposite to the inward direction, the absorber including a water absorbent polymer, wherein: the absorber has, in a crotch portion region applied to a crotch portion of the wearer, a central portion which is formed at a central part of the absorber in the widthwise direction, a pair of side edge portions including a side edge of the absorber in the widthwise direction, and a pair of middle portions which are positioned between the central portion and the side edge portions; at the central portion, a central curve forming portion is formed along the lengthwise direction so that the absorber can be curved to be convex in the inward direction; at each of the middle portions, a side curve forming portion is formed along the lengthwise direction so that the absorber can be curved to be convex in the outward direction; and an average basis weight of the water absorbent polymer at the central portion is smaller than an average basis weight of the water absorbent polymer at the middle portions.

A disposable wearing article comprising an absorber according to the preceding item or any of the foregoing items.

Additionally, one or more of the following embodiments are provided in accordance with further aspects:

Preferably, the average basis weight of the water absorbent polymer at the side edge portions is smaller than the average basis weight of the water absorbent polymer at the middle portions.

The average basis weight of the water absorbent polymer at the side edge portions may be the same as the average basis weight of the water absorbent polymer at the middle portions.

The average basis weight of the water absorbent polymer at the side edge portions may be the same as the average basis weight of the water absorbent polymer at the central portion.

Preferably, the middle portions each include an inside middle portion which is a region from the side curve forming portion to a boundary associated with the central portion in the widthwise direction; the central portion includes a sub-central portion from a boundary associated with a respective one of the middle portions to the central curve forming portion in the widthwise direction; and an average basis weight of the water absorbent polymer at the sub-central portion is less than an average basis weight of the water absorbent polymer at the inside middle portion.

Preferably, the middle portions each include an outside middle portion which is a region from the side curve forming portion to a boundary associated with a respective one of the side edge portions in the widthwise direction; and an average basis weight of the water absorbent polymer at the side edge portion is smaller than an average basis weight of the water absorbent polymer at the outside middle portion.

Preferably, one or both of the middle portions is formed, in the widthwise direction, from a position which corresponds to half of a distance between a center of the central curve forming portion and a center of the side curve forming portions, to a position which corresponds to half of a distance between the center of the side curve forming portion and a side edge of the absorber.

Preferably, in the widthwise direction, a width of the central portion is identical to a width of one or both of the side edge portions.

Preferably, in the lengthwise direction, an average basis weight of the water absorbent polymer in a region positioned outside of the central portion is larger than an average basis weight of the water absorbent polymer at the central portion.

The central portion preferably extends, in the lengthwise direction, across the length of the crotch portion region only, i.e. it is bounded in the lengthwise direction by the inner boundaries of the backside middle inside leg region and the foreside middle inside leg region.

Preferably, a thickness of the absorber in the central portion only, in the side edge portion only, or in both the central portion and the side edge portion is smaller than a thickness of the absorber at the middle portion.

The absorber may have a first layer and a second layer which are superimposed on one another; the central portion and the side edge portion being formed of only the second layer; and the middle portion being formed of the first layer and the second layer. Alternatively, only the central portion is formed of only the first layer; and the middle portion and the side edge portion are formed of the first layer and the second layer.

Preferably, the average basis weight of the water absorbent polymer in the first layer is smaller than the average basis weight of the water absorbent polymer in the second layer.

Preferably, the second layer is positioned at a skin contact surface side with the wearer; and the first layer is positioned at a non-skin contact surface side of the wearer.

Preferably, the central curve forming portion is formed of a central slit which is formed at the absorber along the lengthwise direction, or is formed of a central elastic member which is disposed along the lengthwise direction.

Preferably, the side curve forming portion is formed of a side slit which is formed at the absorber along the lengthwise direction.

The absorber may be provided with a topside covering sheet and a backside covering sheet, which is provided on a non-skin contact surface side of the absorber, wherein the topside covering sheet is bonded to the backside covering sheet at a portion at which one or more slits comprising the central curve forming portion and/or the side curve forming portions are formed.

A thickness of the absorber at the central portion and at each of the side edge portions may be smaller than that of the absorber at the middle portions. Alternatively, the absorber may be thinner at the central portion only. In this case, the thicknesses of the side edge portions and the middle portions may be equal.

A water absorption magnification of the water absorbent polymer at the central portion and the side edge portions may be smaller than that of the water absorbent polymer at the middle portions.

According to the embodiments in the above paragraphs, the features of which may be taken in isolation or in combination with one another, the advantageous effect(s) of the present invention is/are better ensured. Further advantageous effects of the respective embodiments may be obtained as discussed in the respective related descriptions.

Note that this application claims the benefit of Japanese Application No. 2010-043596 the entire disclosure of which is incorporated by reference herein.

The invention claimed is:
1. A disposable wearing article, comprising:
  an absorber having
    a lengthwise direction;
    a widthwise direction which is orthogonal to the lengthwise direction;
    an inward direction which is configured to be oriented toward a wearer; and an outer direction which is oriented to a side opposite to the inward direction, the absorber including a water absorbent polymer, wherein the absorber has, in a crotch portion region configured to be applied to a crotch portion of the wearer,
a central portion formed at a central part of the absorber in the widthwise direction,
a pair of side edge portions including a side edge of the absorber in the widthwise direction, and
a pair of middle portions positioned between the central portion and the side edge portions, at the central portion, a central curve forming portion is formed along the lengthwise direction so as to cause the absorber to be curved and convex in the inward direction in use, and the central curve forming portion comprises a central slit formed at the absorber along the lengthwise direction, at each of the middle portions, a side curve forming portion is formed along the lengthwise direction so as to cause the absorber to be curved and convex in the outward direction in use, and the side curve forming portion comprises a side slit formed at the absorber along the lengthwise direction, an average basis weight of the water absorbent polymer at the central portion is smaller than an average basis weight of the water absorbent polymer at the middle portions, an average basis weight of the water absorbent polymer at the side edge portions is smaller than the average basis weight of the water absorbent polymer at the middle portions, each of the middle portions is formed
from a position corresponding to, in the widthwise direction, a half of a distance between a center of the central slit and a center of the respective side slit
to a position corresponding to, in the widthwise direction, a half of a distance between the respective side slit and a respective side edge of the absorber, each of the middle portions includes an outside middle portion extending, in the widthwise direction, from the respective side curve forming portion to a boundary with the respective side edge portion, the average basis weight of the water absorbent polymer at the side edge portions is smaller than an average basis weight of the water absorbent polymer at the outside middle portions, the absorber has a first layer and a second layer which are superimposed on one another, the central portion and the side edge portions are formed by the second layer but not by the first layer, and the middle portions are formed by both the first layer and the second layer.

2. The disposable wearing article according to claim 1, wherein
the middle portions each further include an inside middle portion extending, in the widthwise direction, from the respective side curve forming portion to a boundary with the central portion,
the central portion includes a pair of sub-central portions each extending, in the widthwise direction, from the boundary with the respective middle portion to the central curve forming portion, and
an average basis weight of the water absorbent polymer at the sub-central portions is less than an average basis weight of the water absorbent polymer at the inside middle portions.

3. The disposable wearing article according to claim 2, wherein, in the widthwise direction, a width of the central portion is identical to a width of one or both of the side edge portions.

4. The disposable wearing article according to claim 1, wherein, in the lengthwise direction, an average basis weight of the water absorbent polymer in a region positioned outside of the central portion is larger than an average basis weight of the water absorbent polymer at the central portion.

5. The disposable wearing article according to claim 1, wherein a thickness of the absorber in any of the central portion and the side edge portions is smaller than a thickness of the absorber at the middle portions.

6. The disposable wearing article according to claim 1, wherein the average basis weight of the water absorbent polymer in the first layer is larger than the average basis weight of the water absorbent polymer in the second layer.

7. The disposable wearing article according to claim 6, wherein:
the second layer is positioned at a skin contact surface side of the absorber; and
the first layer is positioned at a non-skin contact surface side of the absorber.

8. A disposable wearing article, comprising:
an absorber having
a lengthwise direction;
a widthwise direction which is orthogonal to the lengthwise direction;
an inward direction which is configured to be oriented toward a wearer; and
an outer direction which is oriented to a side opposite to the inward direction, the absorber including a water absorbent polymer, wherein the absorber has, in a crotch portion region configured to be applied to a crotch portion of the wearer,
a central portion formed at a central part of the absorber in the widthwise direction,
a pair of side edge portions including a side edge of the absorber in the widthwise direction, and
a pair of middle portions positioned between the central portion and the side edge portions, at the central portion, a central curve forming portion is formed along the lengthwise direction so as to cause the absorber to be curved and convex in the inward direction in use, and the central curve forming portion comprises a central slit formed at the absorber along the lengthwise direction, at each of the middle portions, a side curve forming portion is formed along the lengthwise direction so as to cause the absorber to be curved and convex in the outward direction in use, and the side curve forming portion comprises a side slit formed at the absorber along the lengthwise direction, an average basis weight of the water absorbent polymer at the central portion is smaller than an average basis weight of the water absorbent polymer at the middle portions, an average basis weight of the water absorbent polymer at the side edge portions is smaller than the average basis weight of the water absorbent polymer at the middle portions, each of the middle portions is formed
from a position corresponding to, in the widthwise direction, a half of a distance between a center of the central slit and a center of the respective side slit to a position corresponding to, in the widthwise direction, a half of a distance between the respective side slit and a respective side edge of the absorber, each of the middle portions includes an outside middle portion extending, in the widthwise direction, from the respective side curve forming portion to a boundary with the respective side edge portion, the average basis weight of the water absorbent polymer at the side edge portions is smaller than an average basis weight of the water absorbent polymer at the outside middle portions, and in the lengthwise direction, an average basis weight of the water absorbent polymer in a region positioned outside of the central portion is larger than an average basis weight of the water absorbent polymer at the central portion.

* * * * *